US008430886B2

(12) United States Patent
Rushton et al.

(10) Patent No.: US 8,430,886 B2
(45) Date of Patent: Apr. 30, 2013

(54) INSERTER FOR LOCATING AND IMPACTING AN ACETABULAR CUP

(75) Inventors: Neil Rushton, Cambridge (GB);
Richard Eddy Field, Surrey (GB);
Arnaud AuxEpaules,
Saint-Aubin-sur-Mer (GB); Aude Hibon,
Saint Malo (FR)

(73) Assignee: Howmedica Osteonics Corp., Mahwah, NJ (US)

( * ) Notice: Subject to any disclaimer, the term of this patent is extended or adjusted under 35 U.S.C. 154(b) by 325 days.

(21) Appl. No.: 12/692,748

(22) Filed: Jan. 25, 2010

(65) Prior Publication Data
US 2011/0184423 A1 Jul. 28, 2011

(51) Int. Cl.
*A61B 17/58* (2006.01)
(52) U.S. Cl.
USPC .................................................. 606/91
(58) Field of Classification Search .......... 606/81, 606/89, 91, 99, 100; 623/22.12, 22.21–22.39; 81/126, 127, 128, 150
See application file for complete search history.

(56) References Cited

U.S. PATENT DOCUMENTS

| 5,540,697 | A | 7/1996 | Rehmann et al. |
| 5,571,111 | A | 11/1996 | Aboczky |
| 5,609,646 | A | 3/1997 | Field et al. |
| 6,746,452 | B2 | 6/2004 | Tuke et al. |
| 7,341,593 | B2 | 3/2008 | Auxepaules et al. |
| 7,462,180 | B2 | 12/2008 | Raugel et al. |
| 2007/0173856 | A1* | 7/2007 | Parker ............... 606/99 |

* cited by examiner

*Primary Examiner* — Kevin T Truong
*Assistant Examiner* — Diana S Jones
(74) *Attorney, Agent, or Firm* — Lerner, David, Littenberg, Krumholz & Mentlik, LLP

(57) ABSTRACT

An inserter for locating and impacting an acetabular cup which has an inner bearing surface in a prepared acetabulum. The inserter has a handle carrying an anvil, an impaction head adapted to receive the cup and a retention system for attaching the cup to the inserter. The retention system extends between an actuator in the handle and the impaction head. The actuator is operable to free the retention system from the cup by impacting the anvil.

14 Claims, 6 Drawing Sheets

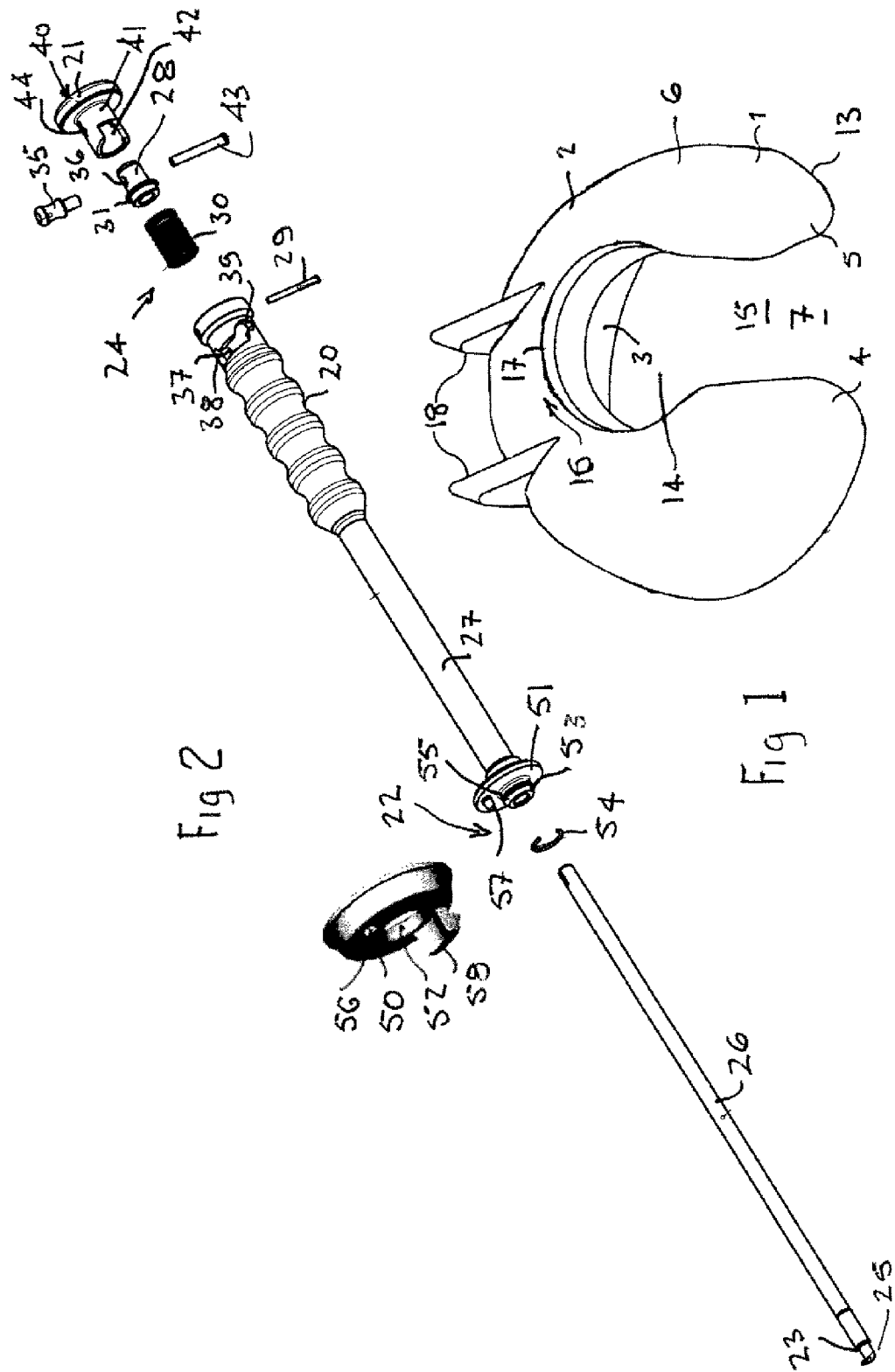

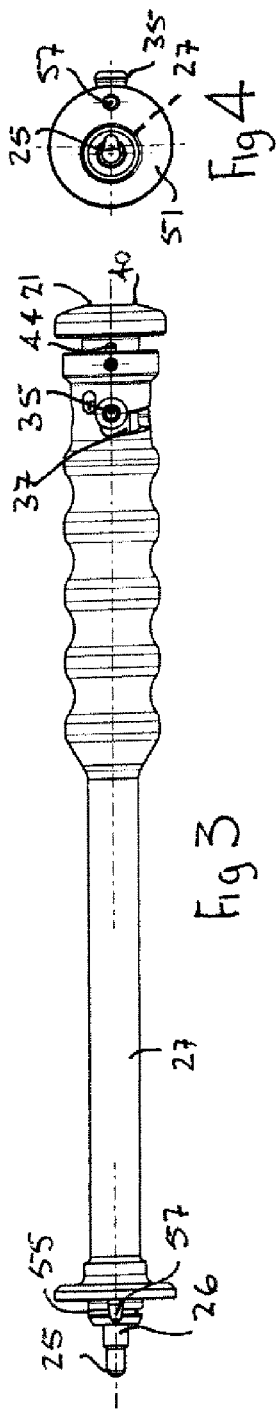
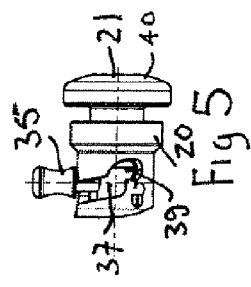
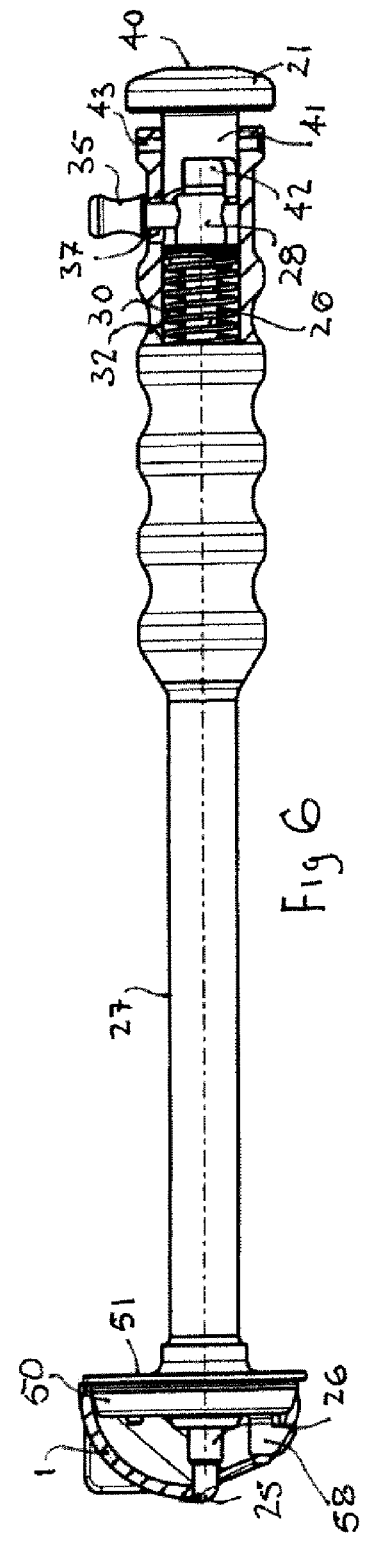

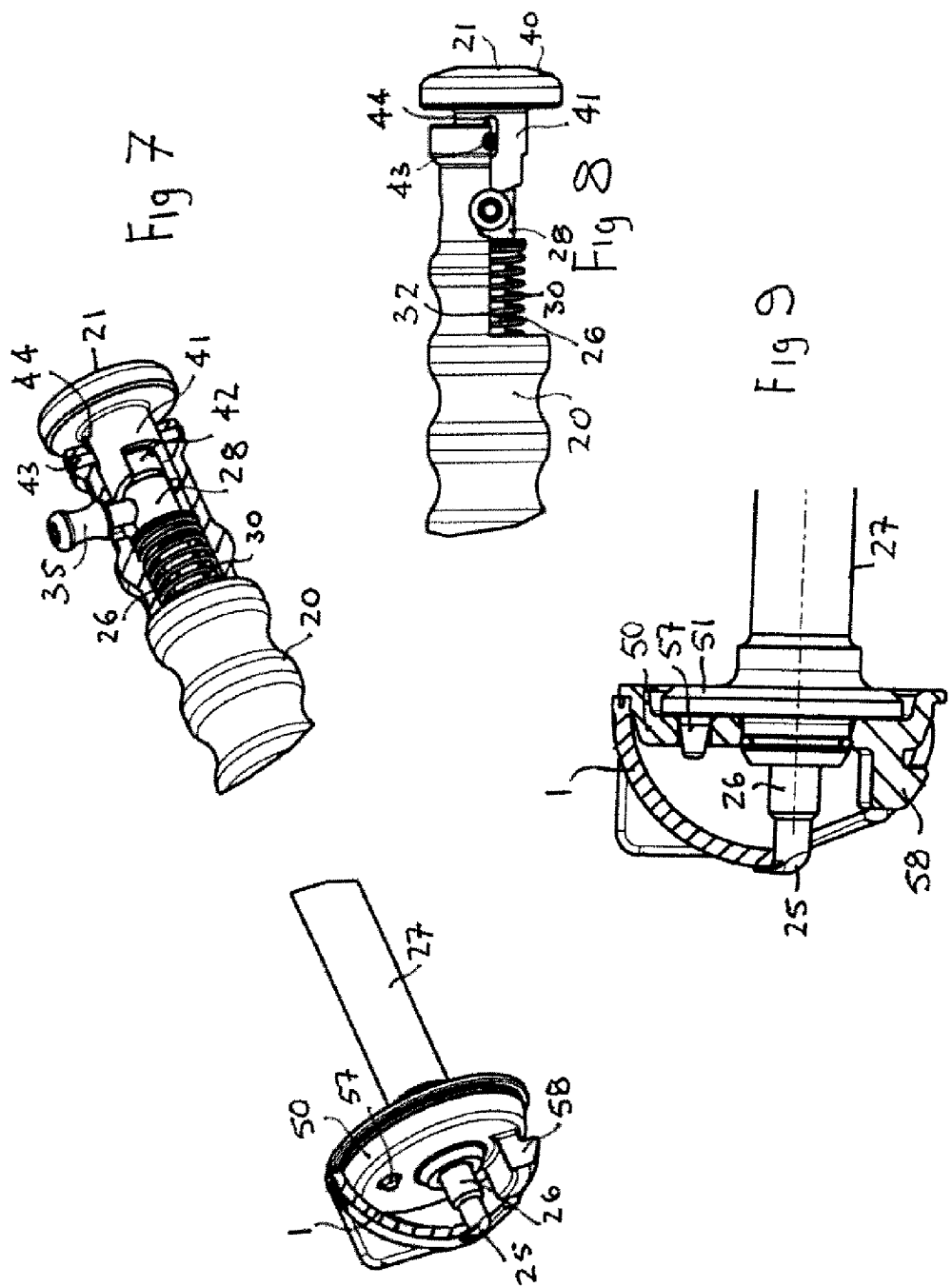

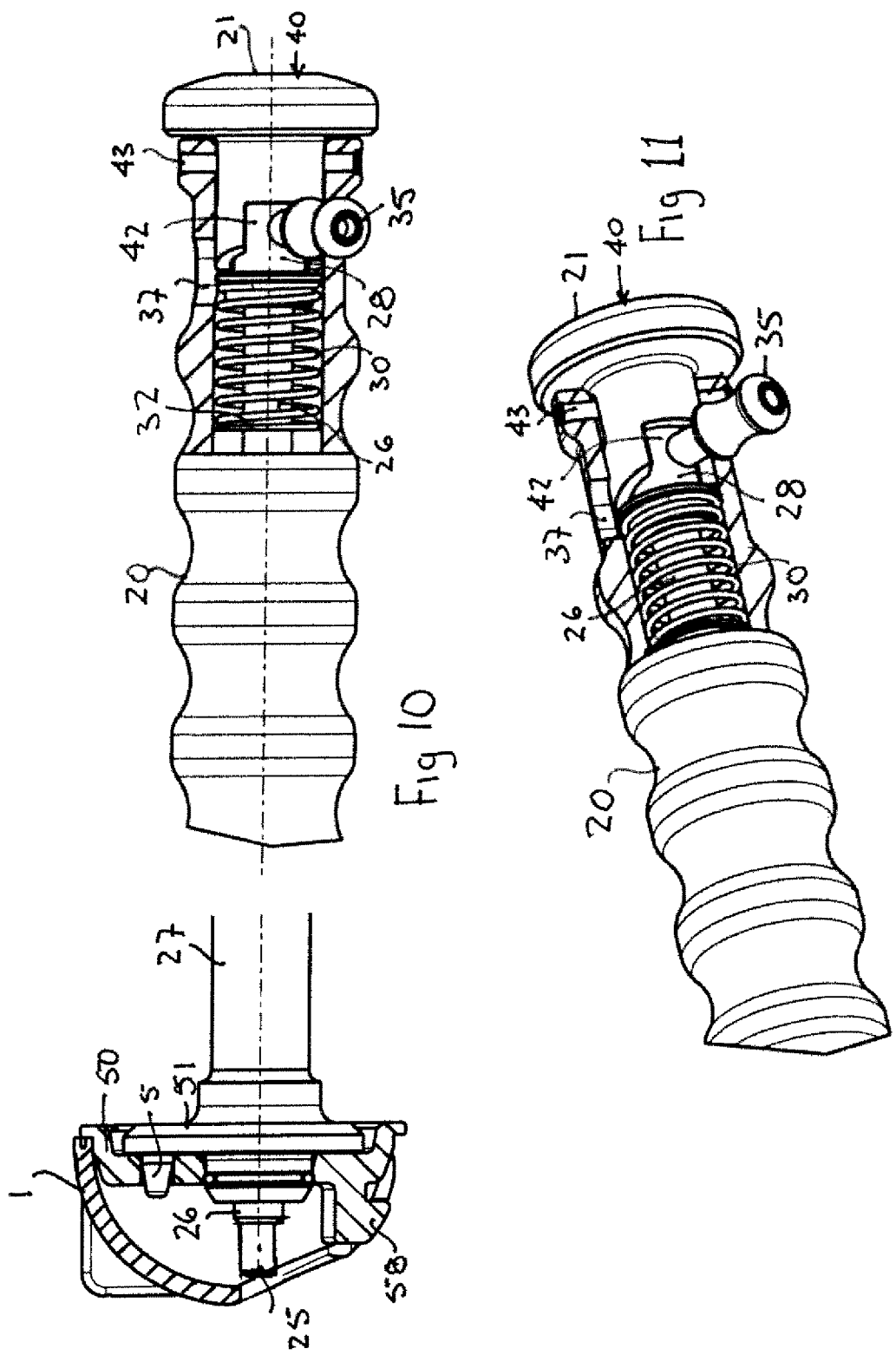

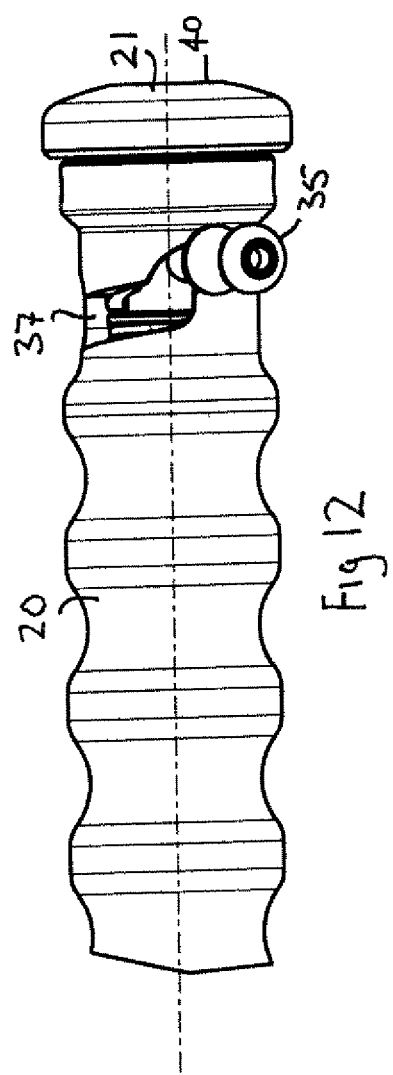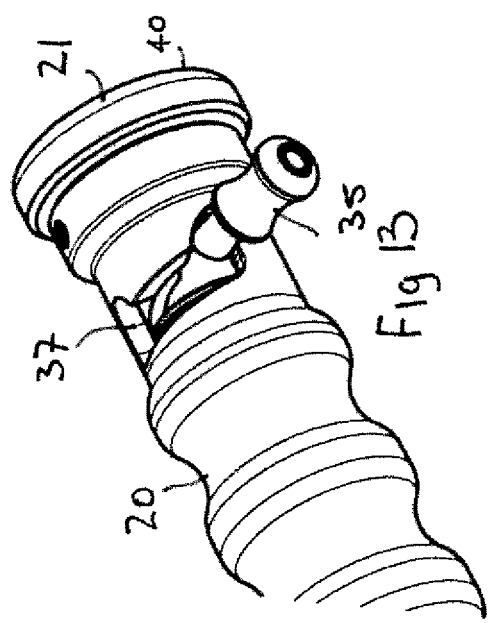

INSERTER FOR LOCATING AND IMPACTING AN ACETABULAR CUP

BACKGROUND OF THE INVENTION

The present invention relates to an inserter for locating and implanting an acetabular cup and is particularly although not exclusively applicable for use with so-called flexible cups. Previous known inserters are usually only designed for use with a particular size of cup and are not adaptable for use with other types of cups. An inserter for a flexible acetabular cup is shown in U.S. Pat. No. 7,462,180, the disclosure of which is incorporated herein by reference.

The present invention is intended to provide a construction which can be used for either holding a cup whilst it is placed in position and which can also be used for impacting the cup into the acetabulum. The invention is also intended to ensure that the inserter is not used to impact the cup whilst it is still attached to the inserter and is constructed so that if the inserter is impacted with the retaining means in place holding the cup the cup will instantly be released.

The instrument is also intended to compensate for deformation of the cup caused by the cups flexibility.

BRIEF SUMMARY OF THE INVENTION

According to the present invention an inserter for locating and impacting an acetabular cup which has an inner bearing surface in a prepared acetabulum comprises a handle carrying an anvil, an impaction head adapted to receive the cup and a retention system for attaching the cup to the inserter extending between an actuator in the handle and the impaction head, and in which the actuator is operable to free the retention system from the cup by impacting the anvil.

Thus, if any attempt is made to use the inserter with the cup attached to it the retention system are immediately released when the anvil is impacted.

In one preferred construction the acetabular cup has an opening in its inner bearing surface at least part of which extends adjacent to or over a substantially central part of the cup and in which in a first position of the actuator the retention system extends into the opening in the inner bearing surface and engage the cup to hold it in position on the impaction head, and in which the actuator can be operated to a second position to free the retention system from the cup by impacting the anvil.

With the above arrangement the opening in the inner bearing surface can extend through the wall of the cup to its outer surface to provide an outer rim which can be engaged by the retention system.

Preferably the actuator can also be operated to free the retaining means independently from the anvil.

The retention system can include a retainer which in the first position of the actuator is raised and engages the outer rim of the opening in the cup and in which in the second position the actuator is rotated and lowered relative to its first position and is clear of and lower than the outer rim.

The retainer can be carried on a rotatable and axially movable elongate operating member which extends between the impaction head and the actuating means in the handle.

With this arrangement a device for resiliently biasing the actuator towards the first and second positions can be provided and can be in the form of a compression spring which acts on said rotatable operating member.

The retention system may conveniently include a projecting finger or hook which in the first position of the actuator extends over or against the side of the opening in the cup and in which in the second position of the actuator is located within or below the opening in the cup.

The actuator can include a control member which projects radially from the side of the handle and which is located in a control slot within which it can move angularly to rotate the retention system, the slot being shaped to cause the retention system to also move axially when rotated. Thus with this arrangement the cup can be locked in position or released by operation of the control member.

The slot can have indentations at each of its ends to locate the control member in the first or second position of the actuator, and the slot is preferably angled towards the end which corresponds to the second position of the actuator.

With the above arrangements the anvil engages the end of the handle when in the second position and thus, when it is used for impacting the cup, the load is carried through the handle to the impaction head.

In an alternative construction, the opening in the inner bearing surface of the cup can be formed with a socket with an inner slot into which the retention system extend to engage and hold the cup in position on the impaction head.

This type of construction can be operated in a similar manner to that described above with regard to constructions in which the opening extends from the inner bearing surface to the outer surface of the cup.

In another alternative construction, the retention system may comprise two or more retention pads which can be operated by the actuator to expand and grip the inner bearing surface of the cup. This construction is particularly adaptable for use with cups which do not have an opening in the inner bearing surface.

The impaction head is arranged so that it can be readily removable from the handle and the invention can therefore include two or more impaction heads of different configurations or size which can be fitted alternatively to the handle.

BRIEF DESCRIPTION OF THE DRAWINGS

The invention can be performed in various ways and some embodiments will now be described by way of example and with reference to the accompanying drawings in which:

FIG. 1 is an isometric view from above of an acetabular cup with an opening extending between its inner bearing surface and its outer surface and which can be used with the inserter according to the invention;

FIG. 2 is an exploded isometric view of the main parts of the inserter according to the invention but not showing the impaction head or the cup with which it is to be used;

FIG. 3 is a plan view of the parts shown in FIG. 2 assembled ready for use;

FIG. 4 is an end view of the inserter shown in FIG. 3;

FIG. 5 is a side view of part of the handle and anvil of the construction shown in FIG. 3;

FIG. 6 is a side view of the construction shown in FIGS. 3 to 5 with the acetabular cup in place and the handle and part of the actuator being shown in cross-section;

FIG. 7 is an isometric view of the inserter shown in FIG. 6 with similar parts in cross-section;

FIG. 8 is a plan view of part of the handle and operating system and anvil of the construction shown in FIGS. 6 and 7;

FIG. 9 is an enlarged side view of the cup and retention means shown in FIG. 7 and which are in FIG. 10 is a side elevation of the construction shown in the previous Figures and in which the actuator and retention system are in a second position in which the cup is released;

FIG. 11 is an isometric view of the anvil and the operating system shown in FIG. 10;

FIG. 12 is an external view of the handle and anvil when in the position shown in FIG. 10;

FIG. 13 is an external isometric view of the handle and anvil with the operating system in the second position as shown in FIG. 11;

DETAILED DESCRIPTION

Figure 14:
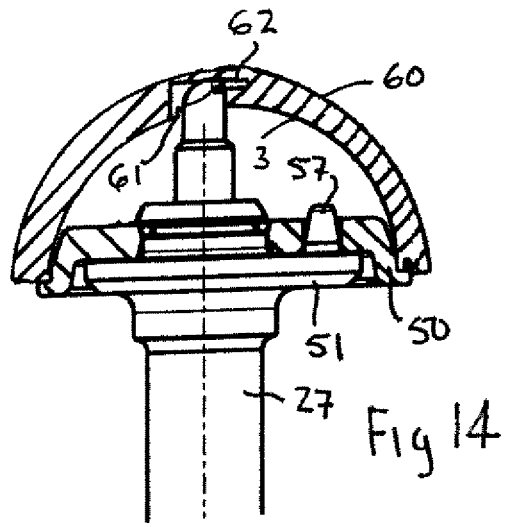
FIG. 14 is a side view of the impaction head of an alternative construction and with the impaction head and cup in cross-section.

FIG. 1 shows a flexible cup with which the construction of an inserter shown in FIGS. 2 to 13 is intended to be used. The cup 1 is of the type shown in European Patent No. 1 205 160 and U.S. Pat. Nos. 5,609,646 and 6,758,864, the disclosures of which are incorporated herein by reference. The cup 1 basically comprises a main portion 2 which has a part-spherical inner bearing surface 3 and there are two independent arms 4 and 5 which extend from the main part 2. The outer surface 6 of the cup is also part-spherical. The arms 4 and 5 are spaced apart to provide a gap or opening 7 between them and the opening breaks out of the cup rim 13.

The main part 14 of the opening 7 is substantially semicircular and has a mouth 15 which provides the interruption in the rim 13 and which is of smaller width than the main part 14 of the opening.

The main part 14 of the opening 7 in the bearing surface 3 which extends adjacent to or over a substantially central part of the cup indicated by reference numeral 16 and extends through the wall of the cup 1 to its outer surface 6 and has an outer rim 17.

The outer surface 2 of the cup carries a pair of projecting fins 18 which extend in spaced apart parallel chordal directions.

The inserter according to the invention for use with the cup shown in FIG. 1 comprises a handle 20 carrying an anvil 21, the impaction head 22 adapted to receive the cup 1 and retention system 23 which extend between actuator 24 in the handle 20 and the impaction head 22, the construction is such that actuator 24 is operable to free the retention system 23 from the cup by impacting the anvil 21.

The retention system 23 includes a retainer 25 in the shape of a projecting finger or hook which is carried on a rotatable axially movable elongate operating member 26 which extends between the impaction head 22 and the actuating means 24 in the handle 20. The handle 20 has a hollow extension 27 through which the elongate operating member 26 extends and enters a flanged sleeve 28 and is held in position by a rivet 29. The handle 20 has an enlarged bore at its outer end in which the end of the elongate operating member 26 is located and in which is provided a coiled compression spring 30 which surrounds the elongate operating member 26. One end of the spring 30 engages a flange 31 on the flanged sleeve 28 and the other end of the spring engages a shoulder 32 which terminates the enlarged portion of the bore in the handle 20. Thus, the spring 30 resiliently biases the elongate operating member 26 towards the impaction head 22.

The flanged sleeve 28 carries a control member in the form of a projecting control lever 35 which is located in an opening 36 in the sleeve 28. The operating member 35 projects radially from the flanged sleeve 28 and extends into a circumferentially extending control slot 37 in the handle 20. The control lever 35 can move angularly to rotate the elongate operating member 26, thus rotating the retention system 23. The slot 37 is shaped to cause the operating member 26 to also move axially when rotated and this is achieved by the slot being angled as is most clearly shown in FIG. 3. The slot 37 has indentations 38 and 39 at each end to locate the control member in those positions.

The anvil 21 has an impacting surface 40 provided on a mushroom shaped head and a hollow sleeve extension 41 one side of which is provided with a cut-out 42 which is large enough to receive the control lever 35. The anvil 40 is held in position in the enlarged part of the bore 31 of the handle by a pin 43 which is located in appropriate openings in the end of the handle 20. The pin 43 passes through an elongate slot 44 in the extension 41 so that the anvil has limited axial movement in the handle 20.

The impaction head 22 comprises a dished circular compaction plate 50 shaped to fit over a flanged mounting 51 on the hollow extension 27 and has a central opening 52 which fits over a boss 53 and is held in position by a circlip 54 which can engage in a circumferential groove 55. The compaction plate 50 also has a location opening 56 which engages a location boss 7 on the flanged mounting 51 to locate its angular position and it also carries a shaped locator 58 which is shaped to locate in the opening 57 of the cup 1.

As will be seen from FIG. 4 the flanged mounting 51 is slightly eccentric in relation to the hollow extension 27 to allow for the retention means 23 to engage the rim 17 of the opening 7 when its lower rim 13 is located on the impaction plate 50, the inner sides of the lower rim 13 engaging the dished side of the plate.

In a first position of the actuator 24 the control lever 35 is in the position shown in FIGS. 3 to 9, i.e. the lever 35 is at one end of the circumferentially extending control slot 37 in the indentation 38 and this will be referred to herein as the "first position". In this position the spring 30 is compressed and the retainer 25 is raised away from the compaction plate 50. It is also in a position where it will engage the rim 17 of the opening 7. If the control lever 35 is moved to its second position which is at the other end of the slot 37 it is biased away from the compaction plate and is located in the indentation 39 and this will be referred to herein as the "second position". In this second position the retainer 25 has been located to a position in which it will not engage the rim 17 of the opening 7 and has also been retracted in relation to the compaction plate 50 so that the inserter can be removed from the cup 1.

In order to locate a cup 1 on the inserter the control lever 35 is first moved to the second position and the cup can be placed over the compaction plate 50 with the rim of the cup located on the rim of the compaction plate and the opening 7 located on the shaped locator 58. The cup's angular location on the inserter is therefore determined. The control lever 35 is now moved manually down the inclined control slot to the first position and this causes the elongate operating member 26 to be rotated and, due to the angulation of the slot to move axially thus raising the retainer 25 and simultaneously locating it to engage the rim 17 of the opening 7. In this first position the retainer 25 is extending away from the opening 7 in the cup and engaging the nearest part of the rim 17 of the opening 7 to hold the cup in position against the rim of the compaction plate 50. The spring is compressed and assists in hold the retainer 25 in place.

The inserter can now be used by a surgeon to accurately place the cup into the prepared acetabulum.

The retainer can now be released from the cup by moving the control lever 35 to the other end of the slot 37 to the second position which thus causes the retainer 25 to be rotated out of contact with the rim 17 and simultaneously lowered within the opening 17 in the cup.

In the first position the axial movement of the elongate operating member 26 causes the anvil 21 to be moved to the right, as shown in the drawings, due to the end of the elongate operating member 26 bearing against the end of the hollow sleeve extension 41. The inserter is constructed so that it is not possible to hammer the cup 1 into place in the prepared acetabulum with the parts in the first position. If the anvil 4 is impacted the control lever 35 is moved from the indentation 38 against the action of the compression spring and the spring then causes the control lever to move along the angled control slot 37 to the second position and to enter indentation 39. This movement to the second position, which is shown in FIGS. 10 to 13, allows the control lever 35 to enter the cut-out 42 in the extension 41 due to the elongate slot 44 through which the pin 43 passes. The effect of the angular movement therefore frees the retainer 25 and frees the inserter from the cup 1. Due to the control lever 35 now being in the cut-out 42 the anvil 21 now moves downwardly and, as shown in FIGS. 10 to 13, engages the end of the handle 20. With the parts being in the second position with the anvil 21 engaging the handle 20 the inserter can be used by hammering the anvil 21 to impact the cup into position, the rim of the cup being engaged by the rim of the compaction plate 50.

The invention therefore provides an inserter which is automatically released from the cup if it is impacted with the inserter attached to the cup.

The operating procedure by the surgeon is therefore to first fit the cup with the control lever 25 in the second position, that is, the released position. The lever 25 is then moved to the first position in which the cup is held in place on the inserter. The surgeon can now insert the cup in the acetabulum as required, with the cup located the control lever 25 is now moved to the second position to release the cup and the anvil 21 can be hammered to impact the cup in place.

If the surgeon fails to release the cup before hammering the anvil 21 the cup will be automatically released by the first hammer blow on the anvil 21.

FIG. 14 shows an alternative construction which can be used with a different type of cup. In this arrangement the cup 60 has an opening 61 which is formed as a socket with a blank end. The inner end of the socket has a radially projecting slot 62. The general construction of the inserter is similar to that described with regard to the previous embodiment but in this arrangement the shaped locator 58 is omitted from the compaction plate 50. The dimensions of the parts are arranged so that the inserter works in the same way as described with regard to the previous embodiment but in which the retainer 25 does not extend through an opening and onto its outer rim but engages within the radial slot 62 provided in the socket 61.

Figure 15:
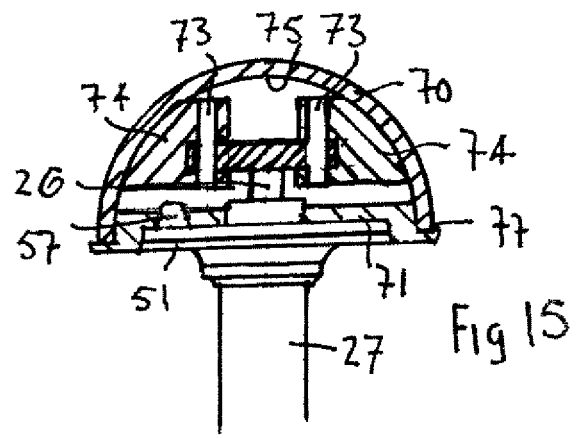
FIG. 15 shows another alternative embodiment of the impaction head which can be used with a cup which does not have an opening between its inner bearing surface and its outer surface; and, FIG. 16 is a plan view of the construction shown in FIG. 15 but with the cup removed.
Figure 16:
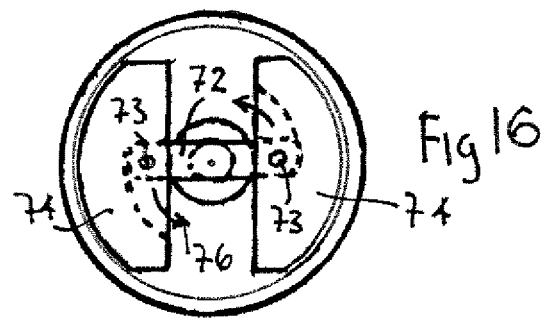

FIGS. 15 and 16 show another construction according to the invention in which the inserter is for use with a cup 70 which does not have an opening in its inner bearing surface. In this arrangement the parts are similar to those set forth in the earlier constructions and the same reference numerals are used to indicate similar parts but the retention means 23 are of a different construction. In this arrangement the elongate operating member 26 carries a bar 72 each radially displaced end of which is provided with a pivot pin 73. Each pin acts to pivotally connect two retention pads 74 which provide the retention system. As will be seen from FIG. 15 the pads are shaped to engage the inner bearing surface 75 of the cup 70.

In FIGS. 15 and 16 the bearing pads are shown with the various parts in the first position, i.e. the bearing pads are engaging the inner bearing surface 75 to lock it to the elongate operating member 26. When the parts are moved to the second position the member 72 is located in the direction of the arrows 76 thus retracting the engagement pads 74 from the inner bearing surface 75 and simultaneously lowering them. In this position the inserter can be released from the cup and, as described above, used for hammering the cup into place in the acetabulum, the load being carried through the handle and directly to the rim 77 of the cup.

The bearing parts can be made from any suitable material, for example aluminium or hardened rubber or a synthetic plastics material.

The moving parts of the inserter can also be made of any suitable metal or synthetic plastics material as appropriate.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An inserter for locating and impacting an acetabular cup which has an inner bearing surface in a prepared acetabulum, comprising a handle carrying an anvil, an impaction head adapted to receive said cup and a retention means for attaching said cup to the inserter, said retention means extending between an actuating means in the handle and the impaction head, said actuating means is operable to free the retention means from the cup by impacting the anvil, wherein the acetabular cup has an opening in its inner bearing surface, at least part of the opening extends adjacent to a substantially central part of the cup, said actuating means having a first position in which the retention means extends into the opening in the inner bearing surface and engages the cup to hold it in position on the impaction head, said actuating means having a second position in which said retention means is freed from the cup by impacting the anvil, wherein the opening in said inner bearing surface extends through a wall of the cup to its outer surface to provide an outer rim, wherein said actuating means can also be operated to free the retaining means independently from said anvil, wherein said retention means include a retainer, and wherein in the first position the retainer is raised and engages the outer rim of the opening in the cup and in the second position the retainer is rotated out of contact with the rim and simultaneously lowered within the opening in the cup.

2. The inserter as claimed in claim 1 in which said retainer is carried on a rotatable and axially movable elongate operating member which extends between the impaction head and the actuating means in the handle.

3. The inserter as claimed in claim 2 including means for resiliently biasing said actuating means towards the first and second positions.

4. The inserter as claimed in claim 3 in which said resilient means for resiliently biasing said actuating means comprises a compression spring which acts on said rotatable operating member.

5. The inserter as claimed in claim 1 in which the retention means includes a projecting finger or hook which in the first position of the actuating means extends over or against the side of the opening in the cup and which in the second position of the actuating means is located within or below the opening in the cup.

6. The inserter as claimed in claim 1 in which the actuating means includes a control member which projects radially from the side of the handle and which is located in a control slot within which it can move angularly to rotate the retention means, said slot being shaped to cause the retention means to also move axially when rotated.

7. The inserter as claimed in claim 6 in which said slot has indentations at each end to locate said control member in the first or second position of the actuating means.

8. The inserter as claimed in claim 6 in which said slot is angled towards the end which corresponds to the second position of the actuating means.

9. The inserter as claimed in claim 1 in which said anvil engages the end of the handle when in the second position.

10. The inserter as claimed in claim 1 in which said opening in said inner bearing surface of the cup is formed as a socket with an inner slot into which the retention means extend to engage and hold the cup in position on the impaction head.

11. The inserter as claimed in claim 1 in which said retention means comprises two or more retention pads which can be operated by the actuating means to expand and grip the inner bearing surface of the cup.

12. The inserter as claimed in claims 1 in which said impaction head is readily removable from said handle.

13. The inserter as claimed in claim 12 which includes two or more impaction heads of different configuration or size which can be fitted alternatively to said handle.

14. An inserter for locating and impacting an acetabular cup in an acetabulum comprising:

a shaft having an anvil coupled to a first shaft end and an impaction head for coupling to an acetabular cup at a second shaft end;

an actuator intermediate the first and second shaft ends, the actuator having a first position wherein the anvil is rigidly connected to the first shaft end and a second position wherein the anvil is connected to the first shaft end by a flexible spring connection, wherein the acetabular cup has an inner bearing surface having an opening therein at least part of which extends adjacent to a substantially central part of the cup, wherein in said first position of said actuator, the impaction head has a retention means extending into the opening in the inner bearing surface and engaging the cup to hold it in position on the impaction head, said actuator having a second position in which said retention means is freed from the cup by impacting the anvil, wherein the opening in said inner bearing surface extends through a wall of the cup to an outer surface to provide an outer rim, said actuator can also be operated to free the retaining means independently from said anvil by rotating the retention means, said retention means include a retainer, wherein in the first position the retainer is raised and engages the outer rim of the opening in the cup and in the second position the retainer is rotated out of contact with the rim and simultaneously lowered within the opening in the cup; and wherein said retainer is carried on a rotatable and axially movable elongate operating member which extends between the impaction head and the actuator in the handle.

\* \* \* \* \*

UNITED STATES PATENT AND TRADEMARK OFFICE
CERTIFICATE OF CORRECTION

PATENT NO. : 8,430,886 B2  
APPLICATION NO. : 12/692748  
DATED : April 30, 2013  
INVENTOR(S) : Neil Rushton et al.

Page 1 of 1

It is certified that error appears in the above-identified patent and that said Letters Patent is hereby corrected as shown below:

In The Specification

Column 2, line 60, after "FIG. 7" delete "and which are in"

In The Claims

Column 7, line 23, "The inserter as claimed in claims" should read --The inserter as claimed in claim--

Signed and Sealed this  
Nineteenth Day of April, 2016

Michelle K. Lee  
*Director of the United States Patent and Trademark Office*